(12) United States Patent
Sribar et al.

(10) Patent No.: US 6,181,765 B1
(45) Date of Patent: Jan. 30, 2001

(54) X-RAY TUBE ASSEMBLY

(75) Inventors: Rok Sribar, Mountain View, CA (US); Vlatko Vlatkovic, Schenectady, NY (US)

(73) Assignee: General Electric Company, Schenectady, NY (US)

( * ) Notice: Under 35 U.S.C. 154(b), the term of this patent shall be extended for 0 days.

(21) Appl. No.: 09/208,874

(22) Filed: Dec. 10, 1998

(51) Int. Cl.$^7$ .......................................... A61B 6/00
(52) U.S. Cl. .............................. 378/10; 378/121
(58) Field of Search ..................... 378/10, 134–135, 378/137, 125, 132, 143–145, 16, 9, 4, 26

(56) References Cited

U.S. PATENT DOCUMENTS

| | | |
|---|---|---|
| 5,125,012 | * 6/1992 | Schittenhelm . |
| 5,483,570 | 1/1996 | Renshaw et al. . |
| 5,652,778 | 7/1997 | Tekriwal . |
| 5,995,584 | * 11/1999 | Bhatt . |

* cited by examiner

Primary Examiner—David P. Porta
Assistant Examiner—Pamela R. Hobden

(57) ABSTRACT

An X-ray tube assembly includes a hermetically-sealed annular frame, spaced apart cathode and anode rings and an electron excitation device. The frame surrounds an exterior central passage for receiving a patient therethrough and has an interior chamber with a vacuum and an X-ray transparent window ring surrounding the central passage. The cathode and anode rings are stationarily mounted to the frame and disposed within the interior chamber. The cathode ring has circumferentially arranged side-by-side filaments each separately excitable by the electron excitation device to cause flow of electrons in an e-beam to a target portion of the anode ring such that an X-ray beam is produced that exits the interior chamber passing through the transparent window ring and that can be moved around the patient disposed within the central passage.

8 Claims, 1 Drawing Sheet

X-RAY TUBE ASSEMBLY

BACKGROUND OF THE INVENTION

The present invention generally relates to X-ray tubes and, more particularly, is concerned with an X-ray tube assembly.

Medical X-ray devices, including those employed in computed tomography, generally contain an X-ray tube. An X-ray tube typically includes a cathode, an anode and a stationary frame surrounding the cathode and anode. The cathode is stationary while the anode rotates relative to the cathode. The surrounding frame contains a vacuum chamber and has an X-ray transparent window. The anode has a target surface which faces the cathode. The cathode emits electrons which strike the target surface of the anode and produce X-rays. Some of the X-rays exit the frame as an X-ray beam through the X-ray transparent window.

Load-carrying bearings are located inside the vacuum chamber between the frame and a stem of the anode. The bearings must be lubricated. The target surface of the anode is heated by the impinging electrons. The heat of the target surface is dissipated by thermal radiation and conduction to the frame. The heated frame is cooled by a liquid coolant, such as oil or water, located between the frame and a surrounding casing.

Thermal management requirements have caused the mass and the speed of rotation of the anode to increase dramatically in recent years which adversely affects the performance of bearings over time. Current X-ray tube designs are close to the limits of X-ray tube bearing technology and to the limits of technology available for thermal management.

Consequently, a need exists for an X-ray tube design which will avoid the problems associated with current X-ray tube designs in terms of bearing technology and thermal management without introducing any new problems in place thereof.

BRIEF SUMMARY OF THE INVENTION

The present invention provides an X-ray tube assembly designed to satisfy the aforementioned need. The X-ray tube assembly of the present invention has no moving parts and, therefore, does not need bearings. The X-ray tube assembly includes a ring-shaped stationary anode and cathode. The X-ray tube assembly has a frame which can be cooled by a liquid. The X-ray tube assembly can also be grounded to allow for water cooling. The frame has an annular configuration providing the X-ray tube assembly with an overall donut shape. The annular configuration of the frame, the stationary anode and cathode rings, and the lack of bearings enables the X-ray tube assembly to overcome the problems associated with the prior art in regard to the limits of X-ray tube bearing technology and of the technology available for thermal management.

In an exemplary embodiment of the present invention, an X-ray tube assembly comprises a hermetically-sealed frame and anode and cathode rings stationarily disposed in the frame. The frame has a substantially curved configuration and surrounds an exterior central passage through the frame for receiving a patient therethrough. The frame defines an interior chamber with a vacuum therein and has an X-ray transparent window ring surrounding and facing the central passage of the frame. The frame has a substantially annular configuration and spans up to 360 degrees.

The cathode ring is mounted to the frame and disposed within the interior chamber. The cathode ring has an electron emitting portion and a first electrical potential. The anode ring is also mounted to the frame and disposed within the interior chamber. The anode ring is spaced apart from the cathode ring and has a target portion and a second electrical potential more positive than the first electrical potential of the cathode ring.

The X-ray tube assembly also comprises means for excitation of electrons from the electron emitting portion of the cathode ring to cause the excited electrons to flow in an e-beam from the electron emitting portion of the cathode ring to the target portion of the anode ring. Impact of excited electrons with the target portion of the anode ring produces an X-ray beam that exits the interior chamber of the frame and passes through the transparent window ring and across the central passage of the frame.

The transparent window ring also spans up to substantially 360 degrees as do the cathode and anode rings. In an example, the transparent window ring is disposed between and radially inwardly of the cathode and anode rings, and the target portion of the anode ring faces the electron emitting portion of the cathode ring. In another exemplary embodiment of the present invention, the electron emitting portion of the cathode ring includes a series of circumferentially arranged side-by-side filaments each separately and consecutively excitable by the electron citation means such that the X-ray beam is movable around the patient disposed within the central passage.

DETAILED DESCRIPTION OF THE INVENTION

Figure 1:
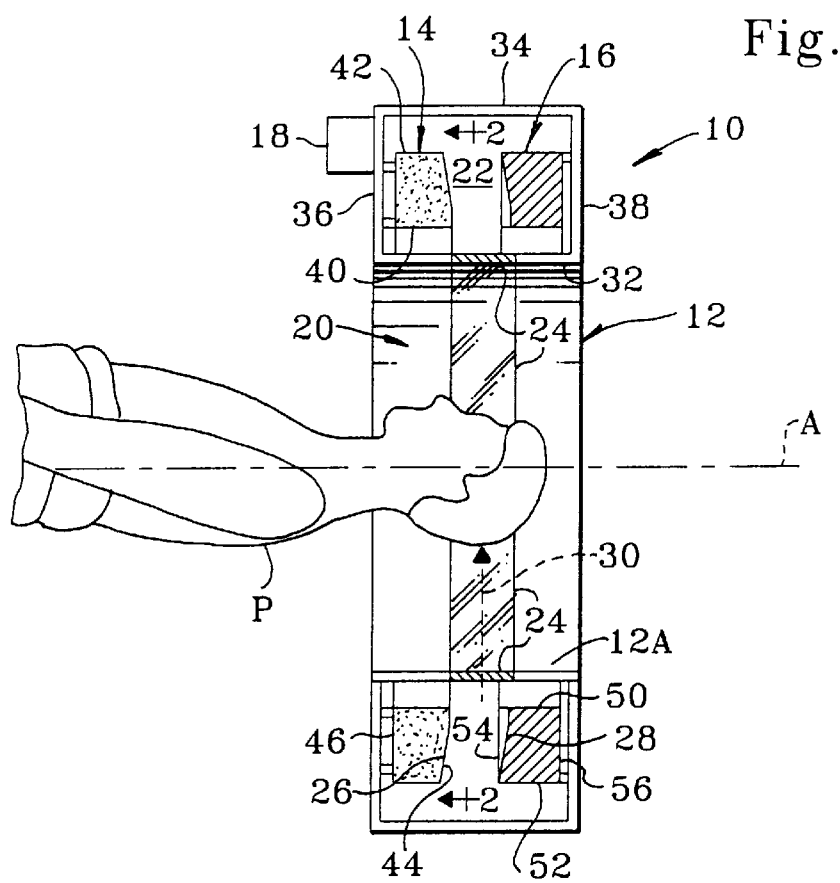
FIG. 1 is a diagrammatic vertical sectional view of an X-ray tube assembly of the present invention.

Referring to the drawings and particularly to FIG. 1, there is illustrated an X-ray tube assembly, generally designated 10, of the present invention. Basically, the X-ray tube assembly 10 includes a hermetically-sealed frame 12, a cathode ring 14, an anode ring 16 and an electron excitation means 18. The frame 12 has a generally curved configuration and surrounds an exterior central passage 20 through the frame 12 for receiving a patient P therethrough. The frame 12 defines an interior chamber 22 with a vacuum therein. The frame 12 also has an X-ray transparent window ring 24 provided about an inner periphery 12A of the frame 12 surrounding and facing the exterior central passage 20.

The cathode ring 14 is fixedly mounted to the frame 12 and disposed within the interior chamber 22 of the frame 12. The cathode ring 14 has an electron emitting portion 26 and a first electrical potential. The anode ring 16 is fixedly mounted to the frame 12 and disposed within the interior chamber 22 of the frame 12 and spaced apart from the cathode ring 14. The anode ring 16 has a target portion 28 facing toward the electron emitting portion 26 of the cathode ring 14 and a second electrical potential more positive than the first electrical potential of the cathode ring 14.

The electron excitation means 18 is connected to the cathode and anode rings 14, 16 and can have a conventional design and be operable in a generally well-known manner to excite electrons from the electron emitting portion 26 of the cathode ring 14. Upon such excitation, the excited electrons are caused to flow in an e-beam from from the electron emitting portion 26 of the cathode ring 14 to the target portion 28 of the anode ring 16 and upon impact therewith produce an X-ray beam 30 that will exit the interior chamber 22 of the frame 12 passing through the transparent window ring 24 of the frame 12 and across the exterior central passage 20.

The frame 12, more particularly, has a size which is generally greater than that of conventional prior art X-ray tube frames. The difference in size is accounted for by the frame 12 replacing much of the gantry found with the conventional prior art X-ray tubes. The frame 12 has a substantially annular configuration and may span up to 360 degrees about a central axis A. The frame 12, however, may span any other suitable angular extent less than 360 degrees. The desired angular extent of the frame 12 may be determined by computer algorithms used for image computation. The frame 12 also has a substantially rectangular cross-sectional configuration, as shown in FIG. 1, but it also may have any other suitable cross-sectional configuration. The frame 12 has an inner side wall 32, an outer side wall 34 and opposite lateral side walls 36, 38. The inner side wall 32 is located at the inner periphery 12A of the frame 12 and surrounds the exterior central passage 20. The frame 12 may be mounted at any suitable location and on any suitable external support structure. The frame 12 can be cooled by a liquid. The assembly 10 can also be grounded to allow for water cooling.

The X-ray transparent window ring 24 is fixedly mounted in the frame 12 and centrally along the inner side wall 32. Furthermore, the transparent window ring 24 is disposed between the cathode ring 14 and the anode ring 16 and radially inwardly therefrom. The transparent window ring 24 is disposed approximately an equal distance from each of the opposite lateral side walls 36, 38 of the frame 12. The transparent window ring 24 may span up to 360 degrees, though it may have any other suitable angular extent less than 360 degrees. The angular extent of the transparent window ring 24 may match or be different than the angular extent of the frame 12. The annular configuration of the transparent window ring 24, compared to the configuration of a traditional X-ray window design, substantially eliminates any local overheating of the X-ray window.

The cathode ring 14 is fixedly mounted to the lateral side wall 36 and the inner side wall 32 of the frame 12 and is disposed within the interior chamber 22 between the lateral side wall 36 and the transparent window ring 24. The cathode ring 14 is spaced from the inner side wall 32, the outer side wall 34 and the lateral side wall 36. The cathode ring 14 can span up to 360 degrees, though it may have any other suitable angular extent less than 360 degrees. The angular extent of the cathode ring 14 may match or be different than the angular extent of the frame 12. The cathode ring 14 also has a substantially rectangular cross-sectional configuration, but it may have any other suitable cross-sectional configuration. The cathode ring 14 has an inner side wall 40, an outer side wall 42 and opposite lateral side walls 44, 46. The electron emitting portion 26 is formed adjacent the lateral side wall 44 of the cathode ring 14. The lateral side wall 44 may be slightly inclined such that the inner side wall 40 has a transverse width slightly greater than a transverse width of the outer side wall 42.

Figure 3:
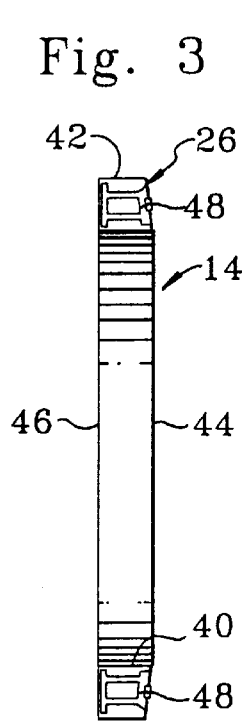
FIG. 3 is a vertical sectional view of the cathode ring taken along line 3—3 of FIG. 2.
Figure 2:
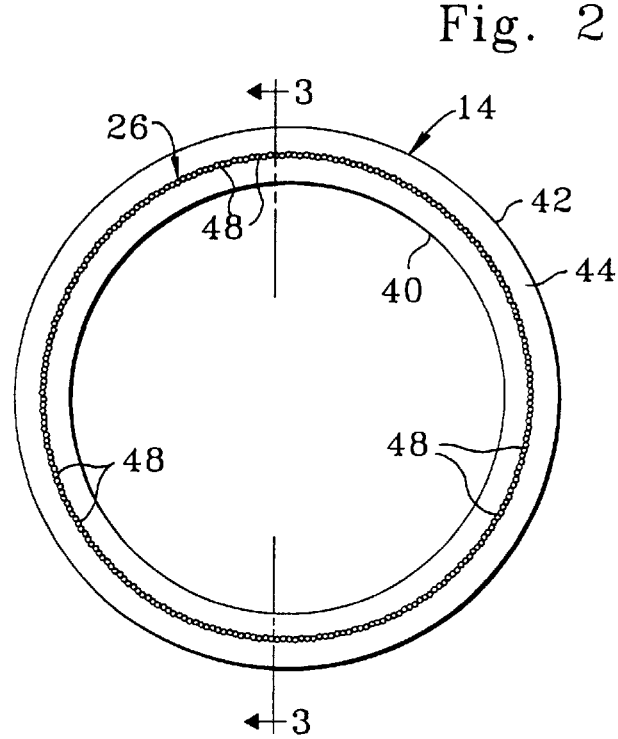
FIG. 2 is a vertical plan view of a cathode ring of the assembly as seen along line 2—2 of FIG. 1 and having a series of circumferentially-arranged side-by-side filaments.

Referring now to FIGS. 2 and 3, the electron emitting portion 26 of the cathode ring 14 includes a series of circumferentially arranged filaments 48 disposed side-by-side one another. The filaments 48 are exposed at the lateral side wall 44 of the cathode ring 14. Each filament 48 is separately connected to and consecutively excitable by the operation of the electron excitation means 18 such that the X-ray beam 30 produced may be moved around the patient P disposed within the central passage 20. The electron excitation means 18 may be connected to any suitable source of AC voltage and may be externally mounted to the lateral side wall 36 of the frame 12. The electron excitation means 18 acts as a controller such that the AC voltage may be applied to any and each of the filaments 48 and such that the X-ray beam 30 is moved around the patient P by the AC voltage being applied to different consecutive filaments 48.

Referring again to FIG. 1, the anode ring 16 is fixed mounted to the lateral side wall 38 and the inner side wall 32 within the interior chamber 22 and between the lateral side wall 38 of the frame 12 and the transparent window ring 24. The anode ring 16 is spaced from the inner side wall 32, the outer side wall 34 and the lateral side wall 36 of the frame 12. The anode ring 16 can span up to 360 degrees, though it may have any suitable angular extent less than 360 degrees. The angular extent of the anode ring 16 may match or be different than the angular extent of the frame 12. The anode ring 16 also has a substantially rectangular cross-sectional configuration, but it may have any other suitable cross-sectional configuration. The anode ring 16 has an inner side wall 50, an outer side wall 52 and opposite lateral side walls 54, 56. The target portion 28 is formed adjacent to the lateral side wall 54 and faces the electron emitting portion 26 of the cathode ring 14.

It is thought that the present invention and its advantages will be understood from the foregoing description and it will be apparent that various changes may be made thereto without departing from the spirit and scope of the invention or sacrificing all of its material advantages, the form hereinbefore described being merely an exemplary embodiment thereof.

What is claimed is:

1. An X-ray tube assembly, comprising:

(a) a hermetically-sealed frame having a substantially curved configuration and surrounding an exterior central passage through said frame for receiving a patient therethrough, said curved frame defining an interior chamber with a vacuum therein and having a X-ray transparent window ring surrounding and facing said central passage;

(b) a cathode ring stationarily mounted to said curved frame and disposed within said interior chamber and having an electron emitting portion and a first electrical potential;

(c) an anode ring stationarily mounted to said curved frame and disposed within said interior chamber and spaced apart from said cathode ring, said anode ring having a target portion and a second electrical potential more positive than said first electrical potential of said cathode ring; and (d) means for excitation of electrons from said electron emitting portion of said cathode ring and to flow in an e-beam therefrom to said target portion of said anode ring and thereby to produce an X-ray beam that exits said interior chamber of said curved frame and passes through said transparent window ring of said curved frame and across said central passage;

(e) said electron emitting portion of said cathode ring including a series of filaments being arranged side-by-side one another circumferentially about said cathode ring, each of said filaments being separately and consecutively excitable by said electron excitation means such that said X-ray beam produced by such consecutive excitation is movable around the patient disposed within said central passage.

2. The assembly of claim 1 wherein said curved frame has a substantially annular configuration and spans up to 360 degrees.

3. The assembly of claim 2 wherein said transparent window ring of said frame spans up to 360 degrees.

4. The assembly of claim 1 wherein said cathode ring spans up to 360 degrees.

5. The assembly of claim 1 wherein said anode ring spans up to 360 degrees.

6. The assembly of claim 1 wherein said transparent window ring is disposed between and inwardly from said cathode ring and said anode ring.

7. The assembly of claim 1 wherein said target portion of said anode ring faces said electron emitting portion of said cathode ring.

8. The assembly of claim 1 wherein said anode ring has a substantially rectangular cross section.

* * * * *